United States Patent [19]

Theodoridis

[11] Patent Number: 4,909,829
[45] Date of Patent: Mar. 20, 1990

[54] SUBSTITUTED QUINOLINONYL AND DIHYDROQUINOLINONYL TETRAZOLINONE HERBICIDES

[75] Inventor: George Theodoridis, Princeton, N.J.

[73] Assignee: FMC Corporation, Philadelphia, Pa.

[21] Appl. No.: 138,981

[22] Filed: Dec. 29, 1987

[51] Int. Cl.⁴ .................... A01N 43/64; C07D 401/04
[52] U.S. Cl. ......................................... 71/92; 546/155; 546/156; 546/157; 546/158
[58] Field of Search ............... 546/155, 156, 157, 158, 546/153; 514/312, 314; 71/92

[56] References Cited

U.S. PATENT DOCUMENTS

| | | |
|---|---|---|
| 4,619,687 | 10/1986 | Haga et al. ............................ 71/92 |
| 4,734,124 | 3/1988 | Chang et al. ............................ 71/92 |

FOREIGN PATENT DOCUMENTS

| | | |
|---|---|---|
| 0176101 | 4/1986 | European Pat. Off. . |
| 61-165383 | 7/1986 | Japan . |

OTHER PUBLICATIONS

Derwent Abstracts, Accession No. 86-235782, Abstract of JP61-165383 (above) Sumitomo Chem. (1985).

*Primary Examiner*—Mukund J. Shah
*Assistant Examiner*—Andrew G. Rozycki
*Attorney, Agent, or Firm*—Robert M. Kennedy; H. Robinson Ertelt; Abner Sheffer

[57] ABSTRACT

Quinolinone compounds of the formula

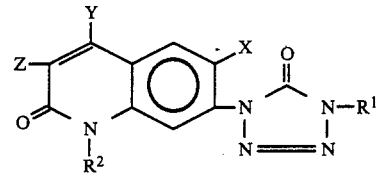

in which $R^2$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy; X is H, halogen, alkyl, or haloalkyl; Y is H, halogen, alkyl, haloalkyl, alkoxycarbonyl, cyano, or nitro; Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro; and $R^1$ is alkyl, alkenyl, alkynyl, haloalkyl, alkoxyalkyl, or haloalkoxyalkyl; and the corresponding 3,4-dihydroquinolinone compounds as herbicides.

27 Claims, No Drawings

SUBSTITUTED QUINOLINONYL AND DIHYDROQUINOLINONYL TETRAZOLINONE HERBICIDES

The invention described in this application pertains to weed control in agriculture, horticulture, and other fields where there is a desire to control unwanted plant growth. More specifically, the present application describes certain herbicidal aryl tetrazolinones, compositions of them, methods of preparing them, and methods for preventing or destroying undesired plant growth by preemergence or postemergence application of the herbicidal compositions to the locus where control is desired. The present compounds may be used to effectively control a variety of both grassy and broadleaf plant species The present invention is particularly useful in agriculture as a number of the compounds described herein show a selectivity favorable to certain crops (e.g. cereal crops or cotton) at application levels which inhibit the growth of or destroy a variety of weeds.

One aspect of this invention relates to tetrazolinones of the following formula I and their use as herbicides:

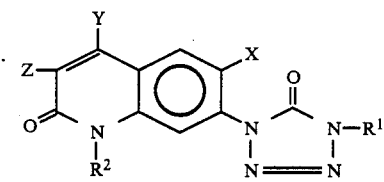

Formula I in which $R^2$ is:
H;
alkyl, e.g. methyl, ethyl, propyl, or isopropyl;
alkenyl, e.g. allyl or methallyl;
alkynyl, e.g. propynyl or methylpropynyl;
haloalkyl, e.g. 3-chloropropyl, 2-fluoroethyl, or 3-fluoropropyl;
alkoxyalkyl, e.g. methoxymethyl or ethoxymethyl;
alkoxyalkoxyalkyl, e.g. ethoxymethoxymethyl;
cycloalkyl, e.g. cyclopropylmethyl;
alkylthioalkyl, e.g. methylthiomethyl;
aralkyl, e.g. benzyl;
cyanoalkyl, e.g. cyanomethyl;
alkoxycarbonylalkyl e.g. methoxycarbonylmethyl;
hydroxy;
or alkoxy, e.g. methoxy or ethoxy.

X is H, halogen (such as F, Cl or Br), alkyl (e.g. methyl), or haloalkyl (e.g. difluoromethyl);

Y is H, halogen (e.g. F, Cl or Br), alkyl (e.g. methyl), haloalkyl (e.g. difluoromethyl), alkoxycarbonyl (e.g. ethoxycarbonyl), cyano, or nitro.

Z is H, halogen (e.g. F, Cl or Br), alkyl (e.g. methyl), haloalkyl (e.g. difluoromethyl), alkoxy (e.g. methoxy), alkenyl (e.g. allyl), alkynyl (e.g. propynyl), haloalkoxy (e.g. difluoromethoxy), alkylthio (e.g. methylthio), alkylsulfinyl (e.g. methylsulfinyl), alkylsulfonyl (e.g. methylsulfonyl), alkoxycarbonyl (e.g. ethoxycarbonyl), cyano, or nitro.

$R^1$ is alkyl (e.g. methyl, alkenyl (e.g. allyl), alknnyl (e.g. propynyl), haloalkyl (e.g. difluoromethyl, 2-fluoroethyl, or 3-fluoropropyl), alkoxyalkyl (e.g. metoxymethyl), or haloalkoxyalkyl (e.g. difluoromethoxymethyl).

In each aspect of the invention it is often preferable that any alkyl, alkenyl, alkynyl or alkylene group or moiety (such as the hydrocarbon moiety of an alkoxy or haloalkoxy group) have up to 6 carbon atoms, e.g. 1 to 4 carbon atoms and any cycloalkyl have 3 to 7 ring carbon atoms.

The compounds of this invention may be prepared by the use of steps generally described in the literature or in the following Example or by methods analogous or similar thereto and within the skill of the art. In the Example below, a compound of the formula

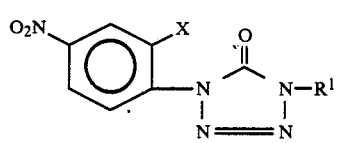

Formula II was reduced to convert the nitro group to an amino group, after which the resulting amino compound was reacted with a compound of the formula YHC=C(-Z)—C(O)—$X^3$ where $X^3$ is, for instance, a lower alkoxy group. This reaction was effected, according to a modification of the known Meerwein reaction involving formation of a diazonium halide and its reaction with an olefin in the presence of a copper halide, to form a compound of the formula

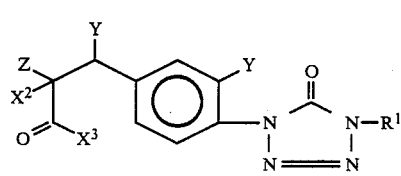

Formula III where $X^2$ is halogen (such as Cl or Br). The resulting compound was then nitrated to form a compound of the formula

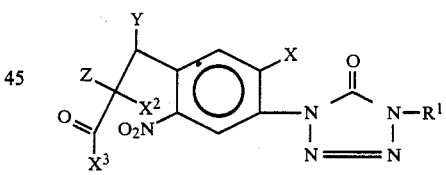

Formula IV

Then, by reaction involving treatment with a iron in an acidified solvent, (e.g. at an elevated temperature such as 40°-150° C.), the nitro group was reduced and ring closure was effected, forming a dihydroquinolinone of the formula

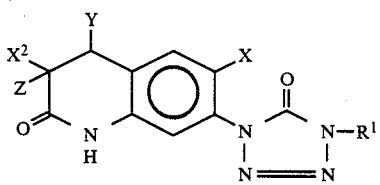

Formula V

The dihydroquniolinone was then dehydrohalogerated, as by treatment with a base such as triethylamine, to form a quinolinone of the formula

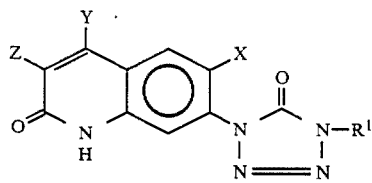

Formula VI

R² groups other than hydrogen may then be introduced by reaction with R²X⁴ wherein X⁴ is a leaving group such as halogen, e.g. Br or I. In the Example below the dehydrohalogenation and treatment with R²X⁴ were effected in a single pot using K₂CO₃ as the base; this resulted in the production of by-products, as described below.

As indicated above, the process involes the use of a reactant of the formula YHC=C(Z)—C(O)—X³. Among the reactants of this type which may be used are the following: methyl acrylate, ethyl acrylate, methyl methacrylate, methyl crotonate, methyl 3-chloroacrylate, methyl 2-methylene-4-pentenoate, and methyl 2-methylene4-pentynoate.

To produce compounds in which R² is hydroxy or alkoxy the reduction and ring closure step may be effected by using a milder reducing agent (such as hydrazine in the presence of rhodium on carbon) to form, during the reaction, an intermediate having an —NHOH group (instead of an —NH₂ group) at the 5-position of the benzene ring so that on cyclization and dehydrohalogenation there is formed a compound having the formula

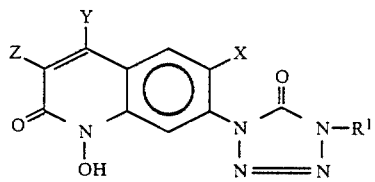

Formula VII after which that compound may be treated with an appropriate alkylating agent in the presence of a base (e.g. methyl iodide in the presence of NaH).

The by-products mentioned above, which also have herbicidal properties, include the corresponding dihydroquinolinones of the formula

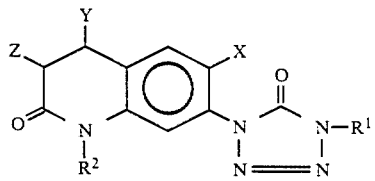

Formula VIII as well as the corresponding quinoline compounds of the formula

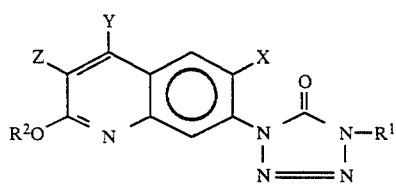

Formula IX

Dihydroquinolinones of formula VIII may also be produced by a catalytic hydrogenation (e.g. under basic conditions) of the above-illustrated quinolinones (e.g. of formula I or VI).

Representative compounds of this invention are tabulated below in Tables 1 and 1A.

The following Example is given to illustrated this invention further. In this application all parts are by weight unless otherwise indicated.

EXAMPLE

1-[1-ETHYL-6-FLUOROQUINOLIN-2(1H)-ONE-7-YL]-4-(3-FLUOROPROPYL)-1,4-DIHYDRO-5H-TETRAZOL-5-ONE

Step A 1-(Fluoro-4-nitrophenyl)-1,4-dihydro-5H-tetrazol-5-one

In a manner similar to that disclosed by O. Tsuge et al, (*J. Org. Chem.*, 45, 5130 (1980)) the reaction of 23.0 g (0.13 mole) of 2-fluoro-4-nitrophenyl isccyanate and 23.0 g (0.20 mole) of rimethylsilyl azide produced 28.3 g of 1-(2-fluoro-4-nitrophenyl)-1,4-dihydro-5H-tetrazol-5-one as a solid m.p. 148°–150° C.

Step B 1-(2-Fluoro-4-nitrophenyl)-4-(3-fluoropropyl)-1,4-dihydro-5H-tetrazol-5-one A stirred mixture of 28.0 g (0.124 mole) of 1-(2-fluoro-4-nitrophenyl)-1,4-dihydro-5H-tetrazol-5-one, 19.3 g (0.140 mole) of potassium carbonate, and 21.8 g (0.140 mole) of 3-fluoropropyl methanesulfonate in 100 mL of dimethylformamide was heated at 60° C. for approximately 18 hours. The reaction mixture was poured into icewater, and the resultant fixture was extracted with diethyl ether. The extract was dried over anhydrous magnesium sulfate and was filtered. The filtrate was evaporated under reduced pressure leaving a residue. This residue was purified by column chromatography on silica gel, eluting with methylene chloride, to yield 21.5 g of 1-(2-fluoro-4-nitrophenyl)-4-(3-fluoropropyl)-1,4-dihydro-5H-tetrazol-5-one as a solid, m.p. 86°–89° C.

Step C

1(4-Amino-2-fluorophenyl)-4-(3-fluoropropyl)-1,4-dihydro-5H-tetrazol-5-one

To a stirred solution of 15.0 g (0.096 mole) of 1-(2-fluoro-4-nitrophenyl)-4-(3-fluoropropyl)-1,4-dihydro-5H-tetrazol-5-one in 200 mL of glacial acetic acid and 10 mL of water, heated at 45° C., was added portionwise 15.0 g (0.27 mole) of iron powder. The reaction mixture was allowed to cool to room temperature and stir for approximately two hours. This mixture was filtered through a pad of Celite filter aid. The filtrate was diluted with 200 mL of water, and the resultant mixture was extracted with diethyl ether. The organic extract was dried over anhydrous magnesium sulfate and was filtered. The filtrate was evaporated under reduced pressure leaving an oil. This oil was purified by column chromatography on silica gel, eluting with methylene chloride, to yield 12.4 g of 1-(4-amino-2-fluorophenyl)-4-(3-fluoropropyl)-1,4-dihydro-5H- tetrazol-5-one as an oil.

The nmr and ir spectra were consistent with the proposed structure.

Step D Methyl 2-chloro-3-[3-fluoro-4-[4-(3-fluoropropyl)-1,4-dihydro-5-oxo-1H-tetrazol-1-yl]-phenyl]propionate To a stirred mixture of 9.0 g (0.035 mole) of 1-(4-amino-2-fluorophenyl)-4-(3-fluoropropyl)-1,4-dihydro-5H-tetrazol-5-one in 9 mL of concentrated hydrochloric acid was added 100 mL of acetone. This mixture was stirred at room temperature for 15 minutes, then was cooled to 8° C. in an ice bath. A solution consisting of 2.5 g (0.036 mole) of sodium nitrate in 40 ml of water was added to the cooled mixture via a submerged addition tube. A nitrogen atmosphere was placed over the reaction mixture and 12.0 g (0.15 mole) of methyl acrylate was added to the reaction vessel. This mixture was stirred for 15 minutes, then (while maintaining a temperature of 5° C.) 0.3 g (0.003 mole) of copper (I) chloride was added portionwise. The resultant mixture was allowed to warm to room temperature and was stirred for about one hour, then poured into ice-water and extracted with diethyl ether. The extract was dried over anhydrous magnesium sulfate and was filtered. The filtrate was evaporated under reduced pressure leaving a residue. This residue was purified by column chromatography on silica gel, eluting with methylene chloride, to yield 8.5 g of methyl 2-chloro-3-[3-fluoro-4-[4-(3-fluoropropyl)-1,4-dihydro-5-oxo-1H-tetrazol-1-yl]phenyl]propionate.

Step E Methyl 2-chloro-3-[5-fluoro-4-[4-(3-fluoropropyl)-1,4-dihydro-5-oxo-1H-tetrazol-1-yl]-2-nitrophenyl]propionate Methyl 2-chloro-3-[3-fluoro-4-[4-(3-fluoropropyl)-1,4-dihydro-5-oxo-1H-tetrazol-1-yl]phenyl]propionate (8.5 g, 0.023 mole) was treated with 2.1 g (0.023 mole) of nitric acid in 60 mL of sulfuric acid to produce 6.5 g of methyl 2-chloro-3-[5-fluoro-4-[4-(3-fluoropropyl)-1,4-dihydro-5-oxo-1H-tetrazol-1-yl]-2-nitrophenyl]propionate as an oil.

The nmr spectrum was consistent with the proposed structure.

Step F 1-(3-Chloro-6-fluoro-3,4-dihydro-quinolin-2(1H)-one-7-yl)-4-(3-fluoropropyl)-1,4-dihydro-5H-tetrazol-5-one To a stirred solution of 6.0 g (0.015 mole) of methyl 2-chloro-3-[5-fluoro-4-[4-(3-fluoropropyl)-1,4-dihydro-5-oxo-1H-tetrazol-1-yl]-2-nitrophenyl]propionate in 100 mL of glacial acetic acid and 8 mL of water was added slowly 6.0 g (0.11 mole) of iron powder. The resultant mixture was stirred at 40° C. for one hour, then filtered, and the filtrate was stirred and heated at reflux for one hour. The reaction mixture was cooled, poured into ice-water, and extracted with diethyl ether. The extract was filtered through a pad of silica gel. The filtrate was evaporated under reduced pressure to yield 3.1 g of 1-(3-chloro-6-fluoro-3,4-dihydroquinolin-2(1H)-one-7-yl)-4-(3-fluoropropyl)-1,4-dihydro-5H-tetrazol-5one as a solid, m.p. 114°–118° C. (Compound B of Table 3 and 4 below).

Step G 1-[1-Ethyl-6-fluoroquinolin-2(1H)-one-7-yl]-4-(3-fluoropropyl)-1,4-dihydro-5H-tetrazol-5-one A solution of 1.8 g (0.0052 mole) of 1-(3-chloro-6-fluoro-3,4-dihydroquinolin-2(1H)-one-7-yl)-4-(3-fluoropropyl)-1,4-dihydro-5H-tetrazol-5-one and 1.1 g (0.0079 mole) of potassium carbonate in 50 mL of dimethylformamide was stirred at room temperature for 30 minutes. To this solution was added 1.6 g (0.011 mole) of 2-iodoethane, and the reaction mixture was stirred at room temperature for one hour, then was heated at 40° C. for two days. The reaction mixture was heated at 70° C. for four hours, then was cooled and poured into icewater. This mixture was extracted with ethyl acetate. The extract was dried over anhydrous magnesium sulfate, filtered, and the filtrate was evaporated under reduced pressure leaving a residue. This residue was purified by column chromatography on silica gel, eluting with ethyl acetate:n-hexane (75:25), to yield 0.77 g of 1[1-ethyl-6-fluoroquinolin-2(1H)-one-7-yl]-4-(3-fluoropropyl)-1,4-dihydro-5H-tetrazol-5-one as an oil.

The nmr spectrum was consistent with the proposed structure.

HERBICIDAL ACTIVITY

The plant test species used in demonstrating the herbicidal activity of compounds of this invention include cotton (*Gossypium hirsutum* var. Stoneville), soybean (*Glycine max* var. Williams), field corn (*Zea mays* var. Agway 595S), wheat (*Triticum aestivium* var. Prodax), rice (*Oryza sativa*), morningglory (*Ipomea lacumosa* or *Ipomea hederacea*), wild mustard (Brassica kaber), velvetleaf (*Abutilon theophrasti*), barnyardgrass (*Echincchloa crus-galli*), green foxtail (*Setaria viridis*), and johnsongrass (*Sorghum halepense*).

Preparation of Flats

Preemergence:

Two disposable fiber flats (8 cm × 15 cm × 25 cm) for each rate of application for each candidate herbicide for preemergence testing are filled to an approximate depth of 6.5 cm with steam sterilized sandy loam soil. The soil is leveled and impressed with a template to provide six evenly spaced furrows 13 cm long and 0.5 cm deep in each flat. Seeds of cotton, soybean, corn, rice and wheat are planted in five of the furrows of the first flat (the sixth furrow is left unplanted), and seeds of wild mustard, morningglory, velvetleaf, barnyardgrass, green foxtail, and johnsongrass are planted in the six furrows of the second flat. The template is again employed to firmly press the seeds into place. A topping soil of equal portions of sand and sandy loam soil is placed uniformly on top of each flat to a depth of approximately 0.5 cm. The flats are first watered, then sprayed with a solution of test compound as described below.

Postemergence:

Two flats for each rate of application for each herbicide candidate are also prepared for postemergence application. The postemergence flats are prepared in the same manner as discussed above for the preemergence flats. The prepared flats are watered for 8–11 days, then the foliage of the emerged tests plants is sprayed with a solution of test compound as described below.

Application of Herbicides

In both the preemergence and postemergnnce tests, the candidate herbicides are applied as aqueous acetone solutions, usually at rates equivalent to 8.0 kilograms/hectare (kg/ha) and/or submultiples thereof, i.e., 4.0 kg/ha, 2.0 kg/ha, and so on.

The four flats (2 preemergence, 2 postemergence) are placed together and sprayed with 30 mL of test solution containing an appropriate amount of the test compound, i.e., approximately 7.5 mL of the test solution is sprayed on each of the four flats. Preemergence applications are made as sprays to the soil surface. Postemergence applications are made as sprays to the foliage. After treatment, the two preemergence flats are watered regularly at the soil surface for approximately 2 weeks, at which time phytotoxicity data are recorded. In the postemergence test the foliage is kept dry for 24 hours after treatment, then watered regularly for approximately 2 weeks, and phytotoxicity data recorded.

Preparation of Test Solutions

For flats of the size described above, an application rate of 8.0 kg/ha of active ingredient is equivalent to 0.06 g of active ingredient/flat (0.24g/4 flats). A stock solution of 0.48 g of the candidate herbicide in 60 mL of a 50:50 mixture of water and acetone containing 0.5% (v/v) of sorbitan monolaurate emulsifier/solubilizer is divided into two 30 mL portions, each containing 0.24 g of the candidate herbicide. For the 8.0 kg/ha application, one of the 30 mL portions is sprayed undiluted onto the four flats (7.5 mL/flat). The remaining 30 mL portion of the stock solution is diluted with an additional 30 mL of the aqueous acetone/emulsifier mixture to provide 60 mL of a solution containing 0.24 g of candidate herbicide. As above, this solution is divided into two 30 mL portions, each containing 0.12 g of candidate herbicide. One of the 30 mL portions is applied, without further dilution, to the four flats for the 4.0 kg/ha rate. The remaining 30 mL portion is further diluted with an equal amount of aqueous acetone/emulsifier mixture, and the resulting 60 mL solution of 0.12 g candidate herbicide is divided into two 30 mL portions each containing 0.06 g of candidate herbicide. One of the 30 mL (0.06 g active) portions is used for the 2.0 kg/ha application rate and the other is used in the preparation of lower rate test solutions by the same serial dilution technique.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

Herbicidal data at selected application rates are given for various compounds of the invention in Tables 3 and 4 below. The test compounds are identified by numbers which correspond to those used in Tables 1and 1A.

In the tables of herbicidal data below, "kg/ha" is kilograms per hectare.

For herbicidal application, the active compounds are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to tee areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solid which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound 17.9 parts of Palmetto clay, and 1.0 part of sodium lignosulfonate and 0.3 part of sulfonated aliphatic polyester as wetting agents. Other wettable powder formulations are:

| Component: | % by Wt. |
|---|---|
| Active ingredient | 40.00 |
| Sodium lignosulfonate | 20.00 |
| Attapulgite clay | 40.00 |
| Total | 100.00 |
| Active ingredient | 90.00 |
| Dioctyl sodium sulfosuccinate | 0.10 |
| Synthetic fine silica | 9.90 |
| Total | 100.00 |
| Active ingredient | 20.00 |
| Sodium alkylnaphthalenesulfonate | 4.00 |
| Sodium lignosulfonate | 4.00 |
| Low viscosity methyl cellulose | 3.00 |
| Attapulgite clay | 69.00 |
| Total | 100.00 |
| Active ingredient | 25.00 |
| Base: | 75.00 |
| 96% hydrated aluminum magnesium silicate | |
| 2% powdered sodium lignosulfonate | |
| 2% powdered anionic sodium alkyl-naphthalenesulfonate | |
| Total | 100.00 |

Frequently, additional wetting agent and/or oil will be added to the tank-mix for postemergence application to facilitate dispersion on the foliage and absorption by the plant.

Other useful formulations for herbicidal applications are emulsifiable concentrates (ECs) which are homogeneous liquid or paste compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

The following are specific examples of emulsifiable concentrate formulations:

| Component: | % by Wt. |
|---|---|
| Active ingredient | 53.01 |
| Blend of alkylnaphthalenesulfonate and polyoxyethylene ethers | 6.00 |
| Epoxidized soybean oil | 1.00 |
| Xylene | 39.99 |
| Total | 100.00 |
| Active ingredient | 10.00 |
| Blend of alkylnaphthalenesulfonate and polyoxyethylene ethers | 4.00 |
| Xylene | 86.00 |
| Total | 100.00 |

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations:

| Component: | % by Wt. |
|---|---|
| Active ingredient | 46.00 |
| Colloidal magnesium aluminum silicate | 0.40 |
| Sodium alkylnaphthalenesulfonate | 2.00 |
| Paraformaldehyde | 0.10 |
| Water | 40.70 |
| Propylene glycol | 7.50 |
| Acetylenic alcohols | 2.50 |
| Xanthan gum | 0.80 |
| Total | 100.00 |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylenic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. The following illustrate specific suspensions:

| | % by Wt. |
|---|---|
| Oil Suspension: | |
| Active ingredient | 25.00 |
| polyoxyethylene sorbitol hexaoleate | 5.00 |
| Highly aliphatic hydrocarbon oil | 70.00 |
| Total | 100.00 |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

Other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. Weed control is achieved at low concentrations of the herbicides of this invention; for instance, compound 7 has given good weed control while permitting growth of rice, corn, and cotton at preemergence application rates such as 0.125–0.25 kg/ha and compound 41 has given good weed control while permitting growth of wheat and rice at postemergence application rates such as 0.004–0.015 kg/ha. For field use, where there are losses of herbicide, larger dosages (e.g. four times the dosage mentioned above) may be employed.

The active herbicidal compounds of this invention may be used in combination with other herbicides, e.g. they may be mixed with, say, an equal or larger amount of a known herbicide such as chloroacetanilide herbicides such as 2-chloro-N-(2,6-diethylphenyl)-N-(methoxymethyl)acetamide (alachlor), 2-chloro-N-(2-ethyl-6-methylphenyl-N-(2-methoxy-1-methylethyl)acetamide (metolachlor), and N-chloroacetyl-N-(2,6-diethylphenyl)glycine (diethatyl-ethyl); benzothiadiazinone herbicides such as 3-(1-methylethyl)-(1H)-2,1,3-benzothiadiazin-4-(3H)-one-2,2-dioxide (bentazon); triazine herbicides such as 6-chloro-N-ethyl-N-(1-methylethyl)-1,3,5-triazine-2,4-diamine (atrazine), and 2-[4-chloro-6-(ethylamino)-1,3,5-triazin-2-yl]amino-2-methylpropanenitrile (cyanazine); dinitroaniline herbicides such as 2,6-dinitro-N,N-dipropyl-4-(trifluoromethyl)-benzene-amine (trifluralin); aryl urea herbicides such as N'-(3,4-dichlorophenyl)-N,N-dimethylurea (diuron) and N,N-dimethyl-N'-[3-(trifluoromethyl)phenyl]urea (fluometuron); and 2-[(2-chlorophenyl)methyl]-4,4-dimethyl-3-isoxazolidinone.

It is apparent that various modifications may be made in the formulation and application of the compounds of this invention without departing from the inventive concepts herein as defined in the claims.

TABLE 1

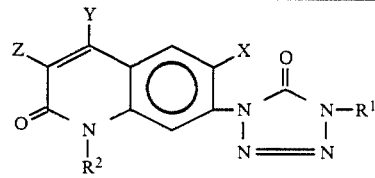

| Cmpd. No. | R$^1$ | R$^2$ | X | Y | Z |
|---|---|---|---|---|---|
| 1 | CH$_3$ | n-C$_3$H$_7$ | F | H | H |
| 2 | C$_2$H$_5$ | n-C$_3$H$_7$ | F | H | H |
| 3 | n-C$_3$H$_7$ | n-C$_3$H$_7$ | F | H | H |
| 4 | CH(CH$_3$)$_2$ | n-C$_3$H$_7$ | F | H | H |
| 5 | CH$_2$CH$_2$F | n-C$_3$H$_7$ | F | H | H |
| 6 | CH$_2$CH$_2$CH$_2$F | CH$_3$ | F | H | H |
| 7 | CH$_2$CH$_2$CH$_2$F | C$_2$H$_5$ | F | H | H |
| 8 | CH$_2$CH$_2$CH$_2$F | n-C$_3$H$_7$ | Cl | H | H |
| 9 | CH$_2$CH$_2$CH$_2$F | n-C$_3$H$_7$ | Br | H | H |
| 10 | CH$_2$CH$_2$CH$_2$F | n-C$_3$H$_7$ | F | H | H |
| 11 | CH$_2$CH$_2$CH$_2$F | n-C$_3$H$_7$ | F | H | Cl |
| 12 | CH$_2$CH$_2$CH$_2$F | n-C$_3$H$_7$ | F | H | Br |
| 13 | CH$_2$CH$_2$CH$_2$F | n-C$_3$H$_7$ | F | H | F |
| 14 | CH$_2$CH$_2$CH$_2$F | n-C$_3$H$_7$ | F | H | CH$_3$ |
| 15 | CH$_2$CH$_2$CH$_2$F | n-C$_3$H$_7$ | F | H | CH(CH$_3$)$_2$ |
| 16 | CH$_2$CH$_2$CH$_2$F | n-C$_3$H$_7$ | F | H | CHF$_2$ |
| 17 | CH$_2$CH$_2$CH$_2$F | n-C$_3$H$_7$ | F | H | CF$_3$ |
| 18 | CH$_2$CH$_2$CH$_2$F | n-C$_3$H$_7$ | F | H | OCH$_3$ |
| 19 | CH$_2$CH$_2$CH$_2$F | n-C$_3$H$_7$ | F | H | OCHF$_2$ |
| 20 | CH$_2$CH$_2$CH$_2$F | n-C$_3$H$_7$ | F | H | SCH$_3$ |
| 21 | CH$_2$CH$_2$CH$_2$F | n-C$_3$H$_7$ | F | H | SO$_2$CH$_3$ |
| 22 | CH$_2$CH$_2$CH$_2$F | n-C$_3$H$_7$ | F | H | NO$_2$ |
| 23 | CH$_2$CH$_2$CH$_2$F | n-C$_3$H$_7$ | F | Cl | H |
| 24 | CH$_2$CH$_2$CH$_2$F | n-C$_3$H$_7$ | F | Br | H |
| 25 | CH$_2$CH$_2$CH$_2$F | n-C$_3$H$_7$ | F | CH$_3$ | H |
| 26 | CH$_2$CH$_2$CH$_2$F | n-C$_3$H$_7$ | F | CHF$_2$ | H |
| 27 | CH$_2$CH$_2$CH$_2$F | n-C$_3$H$_7$ | F | NO$_2$ | H |
| 28 | CH$_2$CH$_2$CH$_2$F | n-C$_3$H$_7$ | CH$_3$ | H | H |
| 29 | CH$_2$CH$_2$CH$_2$F | n-C$_3$H$_7$ | C$_2$H$_5$ | H | H |
| 30 | CH$_2$CH$_2$CH$_2$F | n-C$_3$H$_7$ | CHF$_2$ | H | H |
| 31 | CH$_2$CH$_2$CH$_2$F | n-C$_3$H$_7$ | CF$_3$ | H | H |
| 32 | CH$_2$CH$_2$CH$_2$F | CH(CH$_3$)$_2$ | F | H | H |
| 33 | CH$_2$CH$_2$CH$_2$F | n-C$_4$H$_9$ | F | H | H |
| 34 | CH$_2$CH$_2$CH$_2$F | CH$_2$CH$_2$CH(CH$_3$)$_2$ | F | H | H |
| 35 | CH$_2$CH$_2$CH$_2$F | CH$_2$CH$_2$F | F | H | H |
| 36 | CH$_2$CH$_2$CH$_2$F | CH$_2$CH$_2$CH$_2$F | F | H | H |
| 37 | CH$_2$CH$_2$CH$_2$F | CHF$_2$ | F | H | H |

TABLE 1-continued

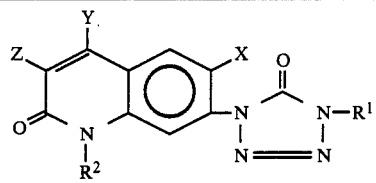

| Cmpd. No. | R¹ | R² | X | Y | Z |
|---|---|---|---|---|---|
| 38 | CH₂CH₂CH₂F | OCH₃ | F | H | H |
| 39 | CH₂CH₂CH₂F | CH₂OCH₃ | F | H | H |
| 40 | CH₂CH₂CH₂F | CH₂CH₂OCH₃ | F | H | H |
| 41 | CH₂CH₂CH₂F | CH₂CH=CH₂ | F | H | H |
| 42 | CH₂CH₂CH₂F | CHCCl=CH₂ | F | H | H |
| 43 | CH₂CH₂CH₂F | CH₂C≡CH | F | H | H |
| 44 | CH₂CH₂CH₂F | CH₂CO₂CH₃ | F | H | H |
| 45 | CHF₂ | n-C₃H₇ | F | H | H |
| 46 | CH₂OCH₃ | n-C₃H₇ | F | H | H |
| 47 | CH₂OCHF₂ | n-C₃H₇ | F | H | H |
| 48 | CH₂CH=CH₂ | n-C₃H₇ | F | H | H |
| 49 | CH₂C≡CH | n-C₃H₇ | F | H | H |
| 50 | CH₂CH₂CH₂F | H | F | H | H |
| 51 | CH₂CH₂CH₂F | CH₂C(CH₃)=CH₂ | F | H | H |
| 52 | CH₂CH₂CH₂F | CH₂OCH₂OC₂H₅ | F | H | H |
| 53 | CH₂CH₂CH₂F | CH₂CHCH₂CH₂ (cyclic) | F | H | H |
| 54 | CH₂CH₂CH₂F | CH(CH₂)₄CH₂ (cyclic) | F | H | H |
| 55 | CH₂CH₂CH₂F | CH₂SCH₃ | F | H | H |
| 56 | CH₂CH₂CH₂F | CH₂C₆H₅ | F | H | H |
| 57 | CH₂CH₂CH₂F | CH₂CN | F | H | H |
| 58 | CH₂CH₂CH₂F | OH | F | H | H |
| 59 | CH₂CH₂CH₂F | n-C₃H₇ | F | F | H |
| 60 | CH₂CH₂CH₂F | n-C₃H₇ | F | CO₂CH₃ | H |
| 61 | CH₂CH₂CH₂F | n-C₃H₇ | F | CN | H |
| 62 | CH₂CH₂CH₂F | n-C₃H₇ | F | H | CH₂CH=CH₂ |
| 63 | CH₂CH₂CH₂F | n-C₃H₇ | F | H | CH₂C≡CH |
| 64 | CH₂CH₂CH₂F | n-C₃H₇ | F | H | S(O)CH₃ |
| 65 | CH₂CH₂CH₂F | n-C₃H₇ | F | H | CO₂C₂H₅ |
| 66 | CH₂CH₂CH₂F | n-C₃H₇ | F | H | CN |

TABLE 1A

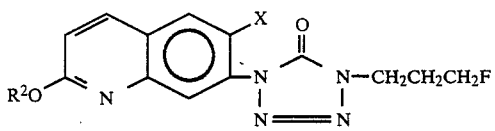

| Cmpd. No. | X | R² |
|---|---|---|
| 1A | F | CH₂CH₃ |
| 2A | F | CH₂CH₂CH₃ |
| 3A | F | CH₂CH=CH₂ |

TABLE 2

| Cmpd No. | M.P. (°C.) | Empirical Formula |
|---|---|---|
| 7 | oil | C₁₅H₁₅F₂N₅O₂ |
| 8 | 103-105 | C₁₆H₁₇F₂N₅O₂ |
| 41 | 76-80 | C₁₆H₁₅F₂N₅O₂ |

TABLE 3

PREEMERGENCE HERBICIDAL ACTIVITY % CONTROL

| | Compound No. | | | | | | |
|---|---|---|---|---|---|---|---|
| | 7 | 8 | 41 | 1A | 2A | 3A | B (Step F) |
| | Rate (kg/ha) | | | | | | |
| Species | 2.0 | 0.250 | 0.250 | 2.0 | 0.5 | 0.50 | 8.0 |
| Cotton | 95 | 0 | 10 | 0 | 0 | 0 | — |
| Soybean | 100 | 0 | 10 | 20 | 0 | 0 | 70 |
| Field Corn | 100 | 10 | 40 | 5 | 5 | 0 | 90 |
| Rice | 80 | 10 | 5 | 5 | 5 | 5 | — |
| Wheat | 100 | 10 | 40 | 10 | 20 | 5 | 60 |
| Morningglory | 80 | 20 | 80 | 10 | 5 | 0 | 90 |
| Wild Mustard | 100 | 10 | 80 | 80 | 0 | 20 | — |
| Velvetleaf | 100 | 90 | 80 | 90 | 40 | 5 | 100 |
| Barnyardgrass | 100 | 50 | 70 | 30 | 50 | 10 | 90 |
| Green Foxtail | 100 | 0 | 20 | 95 | 30 | 10 | 100 |
| Johnsongrass | 95 | 30 | 30 | 10 | 20 | 5 | — |

TABLE 4

| POSTEMERGENCE HERBICIDAL ACTIVITY % CONTROL | | | | | | | |
|---|---|---|---|---|---|---|---|
| | Compound No. | | | | | | |
| | 7 | 8 | 41 | 1A | 2A | 3A | B (Step F) |
| | Rate (kg/ha) | | | | | | |
| Species | 2.0 | 0.250 | 0.250 | 2.0 | 0.5 | 0.50 | 8.0 |
| Cotton | 100 | 100 | 100 | 100 | 90 | 80 | — |
| Soybean | 100 | 90 | 95 | 80 | 50 | 40 | 80 |
| Field Corn | 100 | 70 | 60 | 80 | 60 | 40 | 80 |
| Rice | 90 | 20 | 40 | 5 | 10 | 5 | — |
| Wheat | 95 | 30 | 30 | 10 | 10 | 10 | 40 |
| Morningglory | 100 | 100 | 100 | 95 | 70 | 90 | 100 |
| Wild Mustard | 100 | 100 | 100 | 100 | 90 | 95 | — |
| Velvetleaf | 100 | 100 | 100 | 100 | 100 | 100 | 100 |
| Barnyardgrass | 100 | 90 | 90 | 95 | 20 | 10 | 50 |
| Green Foxtail | 100 | 95 | 90 | 100 | 80 | 10 | 100 |
| Johnsongrass | 95 | — | — | 10 | 40 | — | — |

What is claimed:
1. An herbicidal compound of the formula

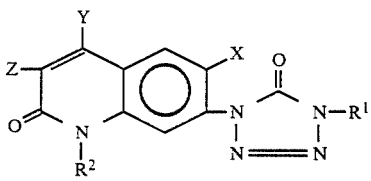

in which:
- $R^2$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy;
- X is H, halogen, alkyl, or haloalkyl;
- Y is H, halogen, alkyl, haloalkyl, alkoxycarbonyl, cyano, or nitro;
- Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro; and
- $R^1$ is alkyl, alkenyl, haloalkyl, alkoxyalkyl, or haloalkoxyalkyl.

2. The herbicidal compound of claim 1 in which any alkyl, alkenyl, or alkynyl group or moiety has up to 6 carbon atoms and cycloalkyl has 3 to 7 ring carbon atoms.

3. The herbicidal compound of claim 2 in which aralkyl is benzyl.

4. The herbicidal compound of claim 3 in which any alkyl, alkenyl, or alkynyl group or moiety has up to 4 carbon atoms.

5. The compound of claim 4 in which $R^1$ is haloalkyl.

6. The compound of claim 5 in which X is halogen.

7. The compound of claim 6 in which Y is H.

8. The compound of claim 7 in which Z is H, halogen, or alkyl.

9. The compound of claim 8 in which $R^2$ is alkyl, allyl, methallyl, propynyl, methylpropynyl, 3-chloropropyl, 2-fluoroethyl, 3-fluoropropyl, 3,3-dichloro-2-propenyl, methoxymethyl, ethoxymethyl, ethoxymethoxymethyl, cyclopropylmethyl, methylthiomethyl, benzyl, cyanomethyl, alkoxycarbonylmethyl, hydroxy, methoxy, or ethoxy.

10. The compound of claim 9 in which $R^2$ is alkyl.

11. The compound of claim 10 in which X is F and Z is H.

12. The compound of claim 11 in which $R^1$ is $CH_2CH_2CH_2F$.

13. The compound of claim 12 in which $R^2$ is n-$C_3H_7$.

14. An herbicidal composition comprising an herbicidally effective amount of the compound of claim 1 in admixture with a suitable carrier.

15. A method for controlling undesired plant growth which comprises applying to the locus where control is desired an herbicidally effective amount of the composition of claim 14.

16. An herbicidal composition comprising an herbicidally effective amount of the compound of claim 2 in admixtue with a suitable carrier.

17. A method for controlling undesired plant growth which comprises applying to the locus where control is desired an herbicidally effective amount of the composition of claim 16.

18. An herbicidal composition comprising an hericidally effective amount of the compound of claim 3 in admixture with a suitable carrier.

19. A method for controlling undesired plant growth which comprises applying to the locus where control is desired an herbicidally effective amount of the composition of claim 18.

20. An herbicidal compound of the formula

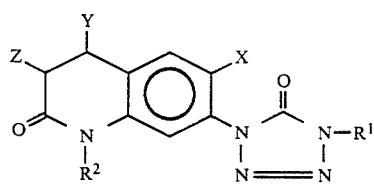

in which:
- $R^2$ is H, alkyl, alkenyl, alkynyl, haloalkyl, haloalkenyl, alkoxyalkyl, alkoxyalkoxyalkyl, cycloalkyl, alkylthioalkyl, aralkyl, cyanoalkyl, alkoxycarbonylalkyl, hydroxy, or alkoxy;
- X is H, halogen, alkyl, or haloalkyl;
- Y is H, halogen, alkyl, haloalkyl, alkoxycarbonyl, cyano, or nitro;
- Z is H, halogen, alkyl, haloalkyl, alkoxy, alkenyl, alkynyl, haloalkoxy, alkylthio, alkylsulfinyl, alkylsulfonyl, alkoxycarbonyl, cyano, or nitro; and
- $R^1$ is alkyl, alkenyl, alkynyl, haloalkyl, alkoxyalkyl, or haloalkoxyalkyl;
- and in which any alkyl, alkenyl, or alkynyl group or moiety has up to 6 carbon atoms and cycloalkyl has 3 to 7 carbon atoms.

21. The compound of claim 20 in which any alkyl, alkenyl, or alkynyl group or moiety has up to 4 carbon atoms and aralkyl is benzyl.

22. The compound of claim 21 in which $R^1$ is $CH_2CH_2CH_2F$, X is F, Y is H or halogen, Z is H, halogen, or alkyl, and $R^2$ is alkyl.

23. The compound of claim 22 in which Y is H, Z is H, and $R^2$ is n-$C_3H_7$.

24. An herbicidal composition comprising an herbicidally effective amount of the compound of claim 20 in admixture with a suitable carrier.

25. A method for controlling undesired plant growth which comprises applying to the locus where control is desired an herbicidally effective amount of the composition of claim 24.

26. An herbicidal composition comprising an herbicidally effective amount of the compound of claim 21 in admixture with a suitable carrier.

27. A method for controlling undesired plant growth which comprises applying to the locus where control is desired an herbicidally effective amount of the composition of claim 26.

* * * * *